US007216650B1

(12) United States Patent
Merriweather et al.

(10) Patent No.: US 7,216,650 B1
(45) Date of Patent: May 15, 2007

(54) HANDCUFFING ASSISTING APPARATUS AND METHOD

(76) Inventors: Michael Merriweather, 9042 Old Creek Dr., Elk Grove, CA (US) 95758; Douglas Wells, 9042 Old Creek Dr., Elk Grove, CA (US) 95758

( * ) Notice: Subject to any disclaimer, the term of this patent is extended or adjusted under 35 U.S.C. 154(b) by 0 days.

(21) Appl. No.: 11/287,440

(22) Filed: Nov. 28, 2005

(51) Int. Cl.
*A61F 5/37* (2006.01)

(52) U.S. Cl. ...................................... 128/879; 119/770

(58) Field of Classification Search ................ 128/869, 128/878, 879; 119/769, 770; 70/16
See application file for complete search history.

(56) References Cited

U.S. PATENT DOCUMENTS

| | | | | |
|---|---|---|---|---|
| 3,545,237 | A * | 12/1970 | Gardella, Jr. et al. | 70/16 |
| 3,740,977 | A | 6/1973 | Stefansen et al. | |
| 4,351,169 | A | 9/1982 | Plymale | |
| 5,007,257 | A | 4/1991 | Thompson | |
| 5,479,943 | A | 1/1996 | Kuhnell, III | |
| D373,446 | S | 9/1996 | Kim et al. | |
| 6,000,249 | A | 12/1999 | Wilber | |
| 6,334,444 | B1 * | 1/2002 | Sisco | 128/869 |

* cited by examiner

*Primary Examiner*—Henry Bennett
*Assistant Examiner*—Camtu Nugyen

(57) ABSTRACT

A handcuffing assisting apparatus includes a panel having a pair of openings extending therethrough. The panel has a break therein extending from a first side edge to a second side edge to define an upper portion and a lower portion of the panel. The upper and lower portions are pivotally coupled together. A closed position is defined when an upper edge of the lower portion is extended into a slot in a lower edge of the upper portion. The break extends through the openings. A securing assembly secures the panel in the closed position. The arms of an inmate are extended through a tray slot of a cell door and into the openings where they are secured by placing the upper and lower portions in the closed position. Handcuffs are then positioned on or removed from the wrists of the inmate.

7 Claims, 4 Drawing Sheets

HANDCUFFING ASSISTING APPARATUS AND METHOD

BACKGROUND OF THE INVENTION

1. Field of the Invention

The present invention relates to handcuffing assisting devices and more particularly pertains to a new handcuffing assisting device for securing an inmate's arms and wrists through a cell door so that handcuffs may safely be positioned on the inmate.

2. Description of the Prior Art

The use of handcuffing assisting devices is known in the prior art. U.S. Pat. No. 5,007,257 describes a device that acts as a safety shield for the positioning of handcuffs on a person's wrists. Other types of prisoner restraint devices include U.S. Pat. No. 6,000,249 as well as U.S. Pat. No. 4,351,169.

While these devices fulfill their respective, particular objectives and requirements, the need remains for a device that is adapted for receiving and securing a prisoner's arms as the arms are extended through a food tray receiving slot of a cell door. This will allow handcuffs to then be placed or removed from the prisoner's wrists without fear that the prisoner will be able to grab and injure a correction officer. Once the handcuffs have been safely positioned over the wrists of the inmate, the device may be removed.

SUMMARY OF THE INVENTION

The present invention meets the needs presented above by generally comprising a panel that has a top edge, a bottom edge, a first side edge, a second edge, a front side and a back side. The panel has a pair of openings therein extending into the front side and outwardly of the back side. The panel has a break therein extending from the first side edge to the second side edge to define an upper portion and a lower portion of the panel. The upper portion has a greater depth than the lower portion. The upper portion has a lower edge has a slot extending therein and an upper edge of the lower portion is positionable in the slot to define a closed position. The upper and lower portions are pivotally coupled together. The break extends through each of the openings. A securing assembly is attached to the panel for selectively securing the panel in the closed position. The arms of an inmate are extended through a tray slot of a cell door and positioned in the openings and the upper and lower portions are placed in the closed position. The upper and lower portions are secured in the closed position. Handcuffs are then positioned on and secured to the wrists of the inmate and the panel removed from the inmate's arms. Alternately, the present invention may be used to remove handcuffs from an inmate's arms by following the reverse procedure.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
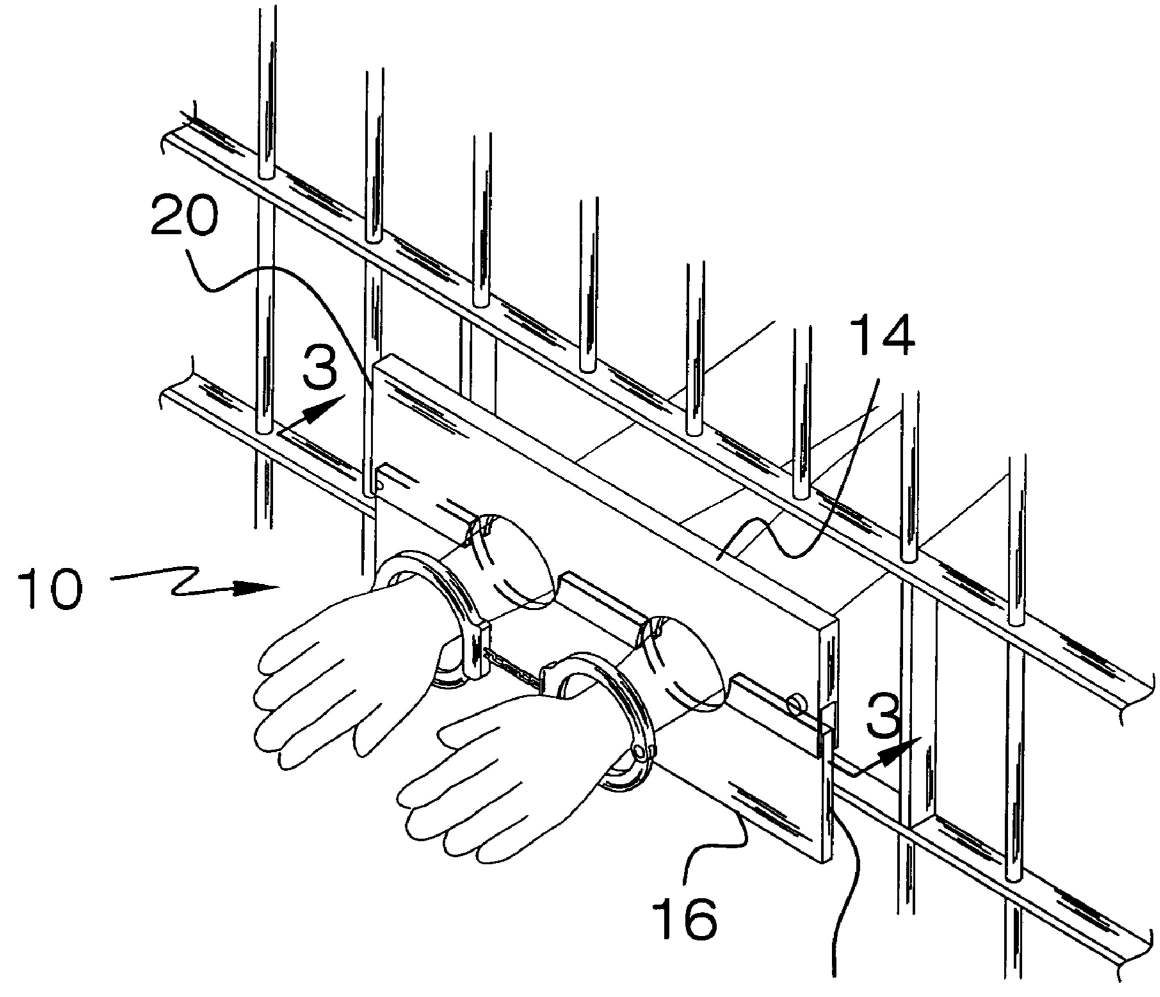
FIG. 1 is a perspective in-use view of a handcuffing assisting apparatus and method according to the present invention.
Figure 2:
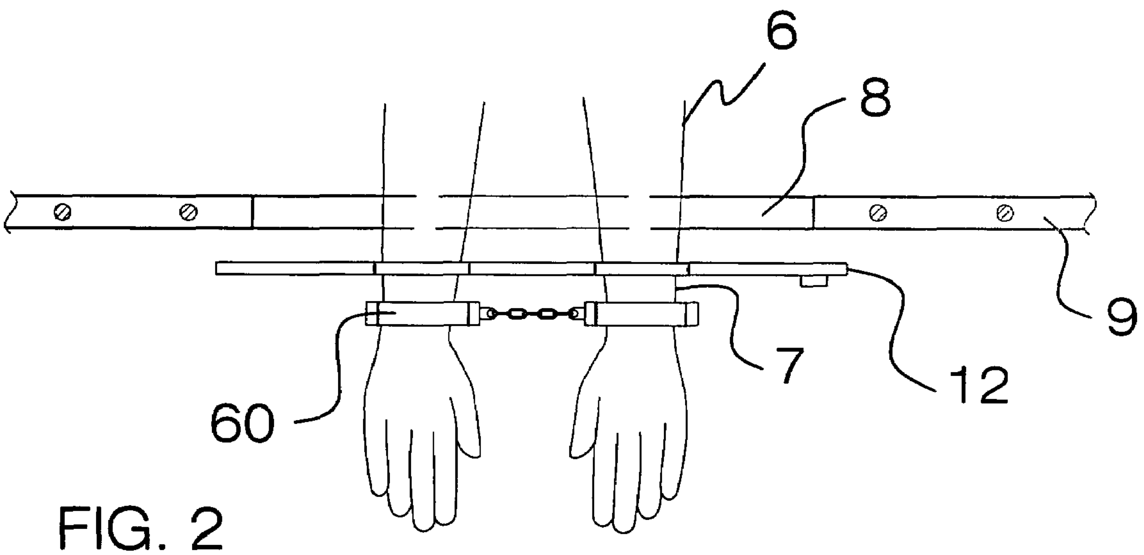
FIG. 2 is a top in-use view of the present invention.
Figure 3:
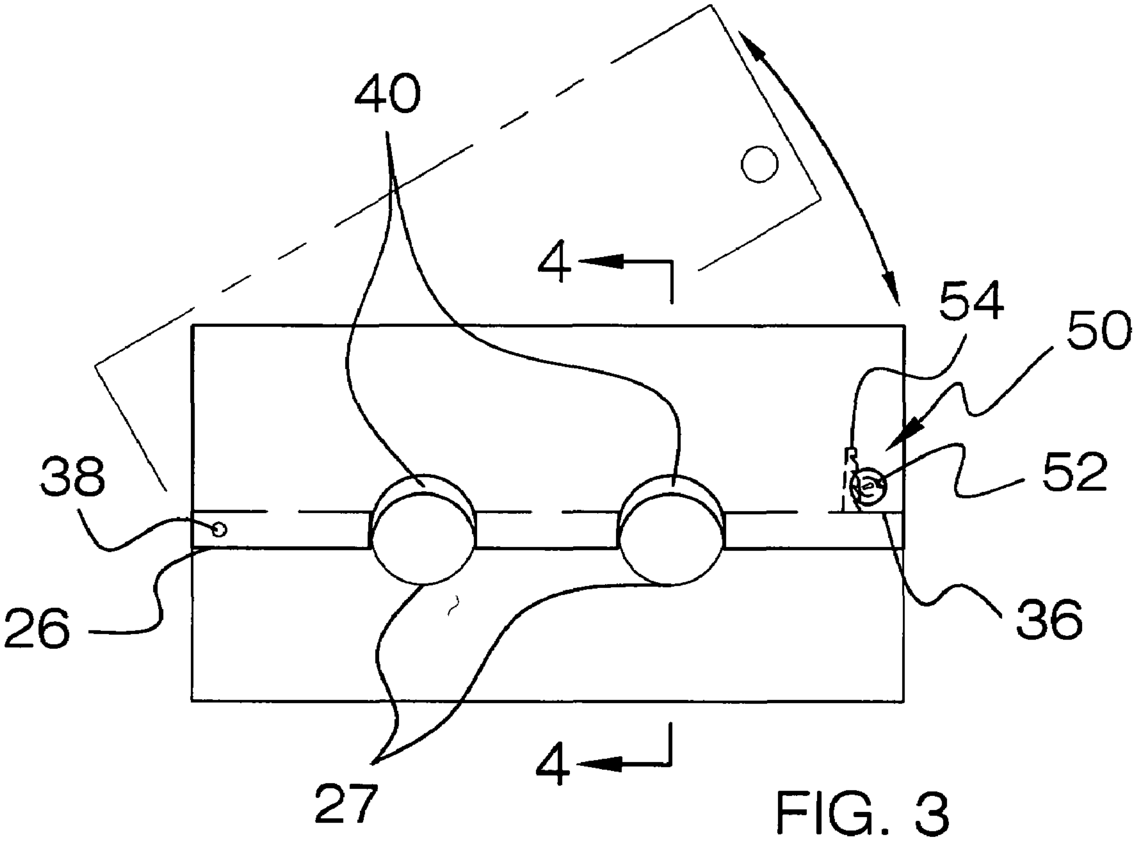
FIG. 3 is a front view of the present invention.
Figure 4:
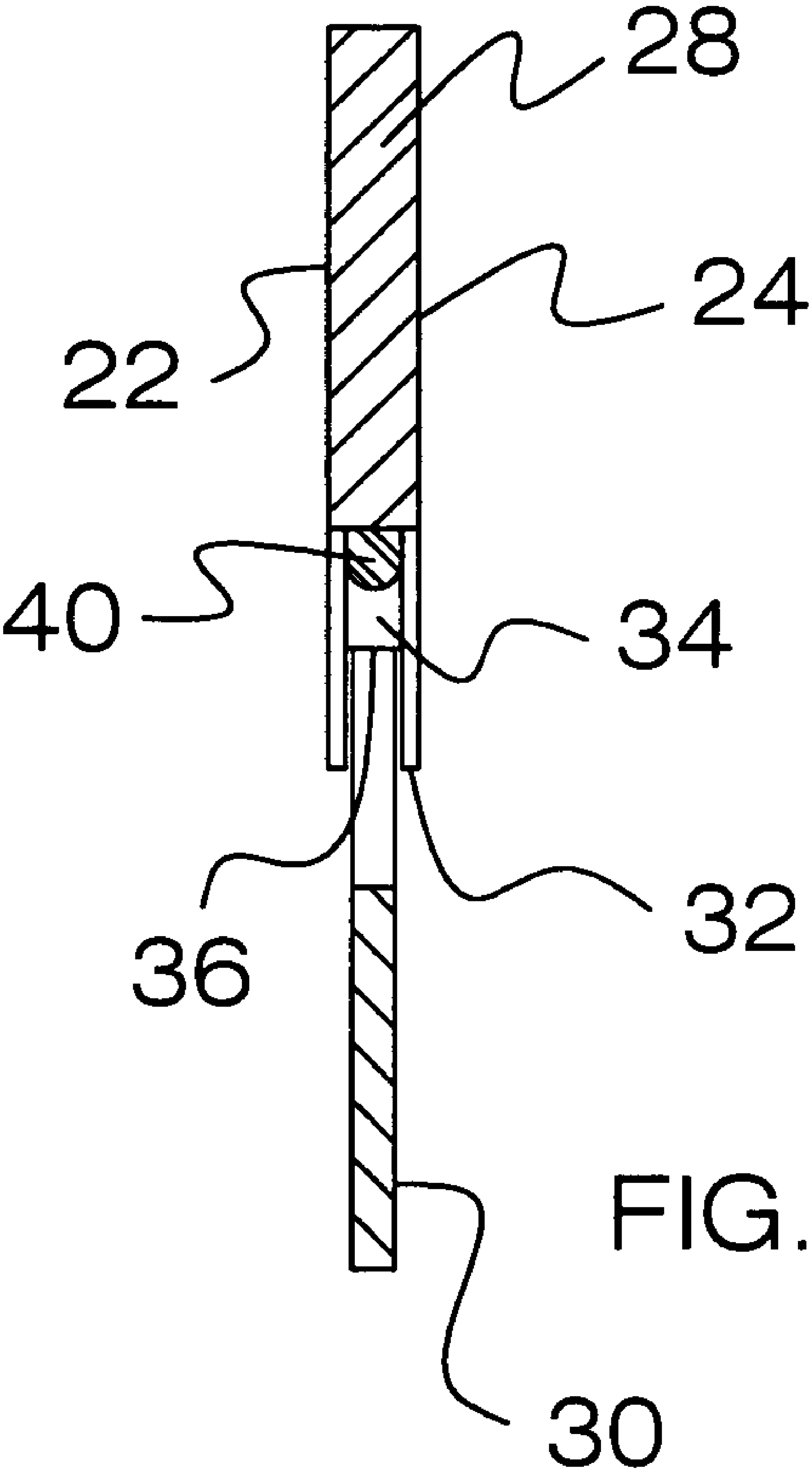
FIG. 4 is a cross-sectional view taken along line 4—4 of FIG. 3 of the present invention.

With reference now to the drawings, and in particular to FIGS. 1 through 4 thereof, a new handcuffing assisting device embodying the principles and concepts of the present invention and generally designated by the reference numeral 10 will be described.

As best illustrated in FIGS. 1 through 4, the handcuffing assisting apparatus and method 10 generally comprises a panel 12 that has a top edge 14, a bottom edge 16, a first side edge 18, a second edge 20, a front side 22 and a back side 24. The panel 12 has a pair of openings 27 therein extending into the front side 22 and outwardly of the back side 24. The panel 12 has a break 26 therein extending from the first side edge 18 to the second side edge 20 and defines an upper portion 28 of the panel and a lower portion 30 of the panel 12. The upper portion 28 has a greater depth than the lower portion 30. The depth of each of the upper 28 and lower 30 portions is preferably between ½ inch and 1 inch. The upper portion 28 has a lower edge 32 having a slot 34 extending therein. An upper edge 36 of the lower portion 30 is positionable in the slot 34 to define a closed position. The upper 28 and lower 30 portions are pivotally coupled together by a pivot rod 38. The break 26 extends through each of the openings 27. The panel 12 is comprised of a rigid material that may include a plastic, a wood material or a metallic material.

The openings 27 each have a generally round shape and a diameter generally between 2.50 inches and 3.50 inches when the upper 28 and lower 30 portions are in the closed position. The openings 27 are horizontally aligned with each other and are spaced between 1 inch and 4 inches apart from each other and each of the openings 27 is spaced at least 4 inches away from each of the first and second side edges. The panel 12 has a width from the first side edge 18 to the second side edge 20 generally between 18 inches and 22 inches and a height generally between 10 inches and 14 inches. A cushioning material 40, such as a foamed elastomer, is attached to and extends along an upper edge of each of the openings 27.

A securing assembly 50 is attached to the panel 12 for selectively securing the panel 12 in the closed position. The securing assembly 50 may include a conventional lock 52 or pawl mounted in the upper portion 28 that is positioned for engaging a toothed plate 54 in the lower portion 30.

In use, the arms 6 of an inmate are extended through a tray slot 8 of a cell door 9. The arms 6 are then positioned in the openings 27 and the upper 28 and lower 30 portions are placed in the closed position so that the inmate's arms 6 are secured in the panel 12. The upper 28 and lower 30 portions are then secured in the closed position with the securing assembly 50. Handcuffs 60 are positioned on and secured to the wrists 7 of the inmate and the panel 12 is removed from the inmate's arms 6. The size of the panel 12 and the positioning of the openings 27 allow the handcuffs 60 to placed on the inmate's wrists 7 without fear of the inmate being able to grab the correctional officer. It should be understood that the reverse procedure may also be followed wherein an inmate is placed in a cell with handcuffs 60 already positioned on the arms 6 of the inmate. The inmate will extend his or her arms 6 through the cell door and the upper 28 and lower 30 portions attached to the arms 6 while the handcuffs are removed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A method of handcuffing an inmate, said method comprising the steps of:

- providing a panel having a top edge, a bottom edge, a first side edge, a second edge, a front side and a back side, said panel having a pair of openings therein extending into said front side and outwardly of said back side, said panel having a break therein extending from said first side edge to said second side edge and defining an upper portion of said panel and a lower portion of said panel, said upper portion having a greater depth than said lower portion, said upper portion having a lower edge having a slot extending therein, an upper edge of said lower portion being positionable in said slot to define a closed position, said upper and lower portions being pivotally coupled together, said break extending through each of said openings;
- providing a securing assembly attached to said panel for selectively securing said panel in said closed position;
- extending arms of an inmate through a tray slot of a cell door;
- positioning the arms into said openings and placing said upper and lower portions in said closed position;
- securing said upper and lower portions in said closed position;
- positioning and securing handcuffs to wrists of the inmate; and
- removing the panel from the arms.

2. The method according to claim 1, wherein each of said openings has generally a round shape and a diameter generally between 2.50 inches and 3.50 inches when said upper and lower portions are in said closed position.

3. The method according to claim 1, wherein said openings are horizontally aligned with each other and are spaced between 1 inch and 4 inches apart from each other.

4. The method according to claim 3, wherein each of said openings is spaced at least 4 inches away from each of said first and second side edges.

5. The method according to claim 4, wherein said panel has a width from said first side edge to said second side edge generally between 18 inches and 22 inches and a height generally between 10 inches and 14 inches.

6. The method according to claim 1, further providing a cushioning material being attached to and extending along an upper edge of each of said openings.

7. A method of handcuffing an inmate, said method comprising the steps of:

- providing a panel having a top edge, a bottom edge, a first side edge, a second edge, a front side and a back side, said panel having a pair of openings therein extending into said front side and outwardly of said back side, said panel having a break therein extending from said first side edge to said second side edge and defining an upper portion of said panel and a lower portion of said panel, said upper portion having a greater depth than said lower portion, said upper portion having a lower edge having a slot extending therein, an upper edge of said lower portion being positionable in said slot to define a closed position, said upper and lower portions being pivotally coupled together, said break extending through each of said openings, each of said openings having a generally round shape and a diameter generally between 2.50 inches and 3.50 inches when said upper and lower portions are in said closed position, said openings being horizontally aligned with each other and being spaced between 1 inch and 4 inches apart from each other, each of said openings being spaced at least 4 inches away from each of said first and second side edges, said panel having a width from said first side edge to said second side edge generally between 18 inches and 22 inches and a height generally between 10 inches and 14 inches, a cushioning material being attached to and extending along an upper edge of each of said openings;
- providing a securing assembly attached to said panel for selectively securing said panel in said closed position;
- extending arms of an inmate through a tray slot of a cell door;
- positioning the arms into said openings and placing said upper and lower portions in said closed position;
- securing said upper and lower portions in said closed position;
- positioning and securing handcuffs to wrists of the inmate; and
- removing the panel from the arms.

* * * * *